United States Patent [19]

Clark et al.

[11] Patent Number: 5,460,045
[45] Date of Patent: Oct. 24, 1995

[54] ULTRASONIC PROBES FOR INSPECTION OF REACTOR PRESSURE VESSEL BOTTOM HEAD AND WELD BUILDUP THEREON

[75] Inventors: Jack P. Clark; Balasubramanian S. Kowdley, both of San Jose; James C. S. Tung, Santa Clara; David C. Berg, San Jose, all of Calif.

[73] Assignee: General Electric Company, Schenectady, N.Y.

[21] Appl. No.: 105,193

[22] Filed: Aug. 9, 1993

Related U.S. Application Data

[62] Division of Ser. No. 865,507, Apr. 9, 1992, Pat. No. 5,272,734.

[51] Int. Cl.$^6$ ............ G01N 29/10; G01N 29/26
[52] U.S. Cl. ............ 73/622; 73/625; 73/628; 376/249; 367/104
[58] Field of Search ............ 73/620, 621, 622, 73/625, 628, 635, 641, 623; 376/249; 367/104, 88

[56] References Cited

U.S. PATENT DOCUMENTS

| | | | |
|---|---|---|---|
| 3,901,073 | 8/1975 | Dent et al. | |
| 4,117,733 | 10/1978 | Gugel | 376/249 |
| 4,131,018 | 12/1978 | Müller et al. | 73/623 |
| 4,149,932 | 4/1979 | Jacobs et al. | 376/249 |
| 4,440,339 | 4/1984 | Tamai et al. | 376/203 |
| 4,577,507 | 3/1986 | Jestrich et al. | 73/640 |
| 4,586,379 | 5/1986 | Burlchardt, Jr. | 73/622 |
| 5,118,464 | 6/1992 | Richardson et al. | 376/245 |
| 5,145,637 | 9/1992 | Richardson et al. | 376/249 |
| 5,173,882 | 12/1992 | Watson | 367/104 |
| 5,196,160 | 3/1993 | Porowski | 376/260 |

Primary Examiner—Hezron E. Williams
Assistant Examiner—Rose M. Finley
Attorney, Agent, or Firm—James E. McGinness

[57] ABSTRACT

An improved method for repair of incore-instrumentation-housing and related defects in a nuclear reactor system involves three stages, each with ultrasonically assisted inspections. In the first stage, a defective incore housing is removed and the exposed area and aperture at the former location of the incore housing is ultrasonically inspected using an ultrasonic probe with a tiltable disk-shaped head that self-conforms to the local contour of the reactor vessel bottom. In the second stage, a weld buildup is formed. The reactor is then sealed and the weld buildup is machined to define an aperture therethrough. The weld buildup is then ultrasonically inspected with a second probe with a centering member that is stationary as the probe body is moved vertically relative to it. In the third stage, a J-prep is formed. A new incore housing is inserted through the weld buildup aperture. The new incore housing is welded at the J-prep. The J-weld is ultrasonically inspected using a third ultrasonic probe. The new incore housing is then connected to the incore guide tube with shrink couplings, and reactor activity can be restored.

6 Claims, 11 Drawing Sheets

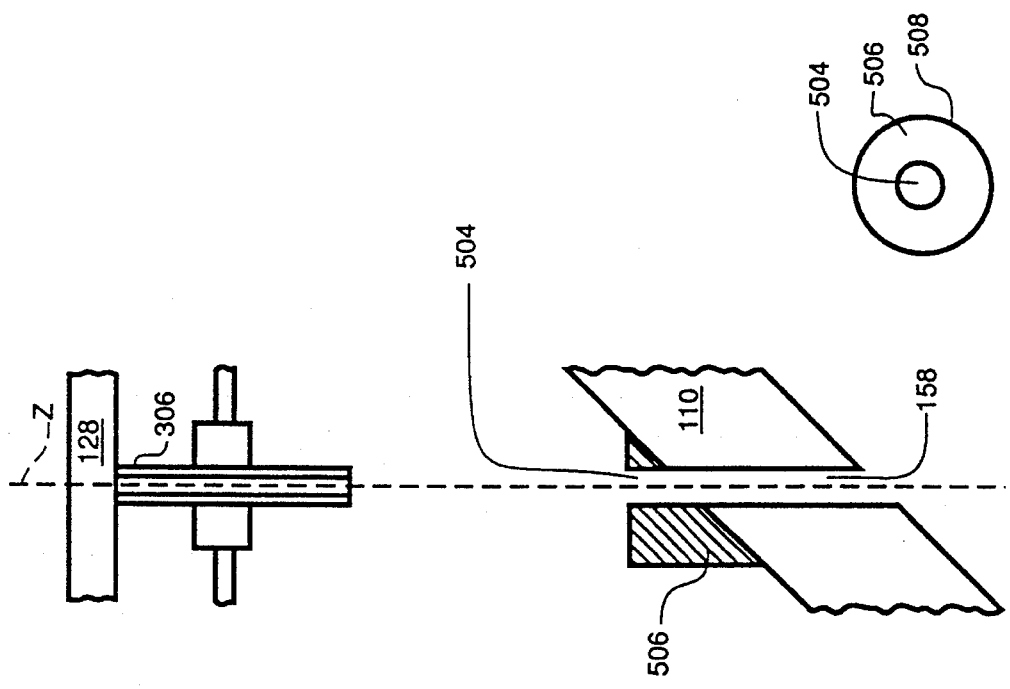
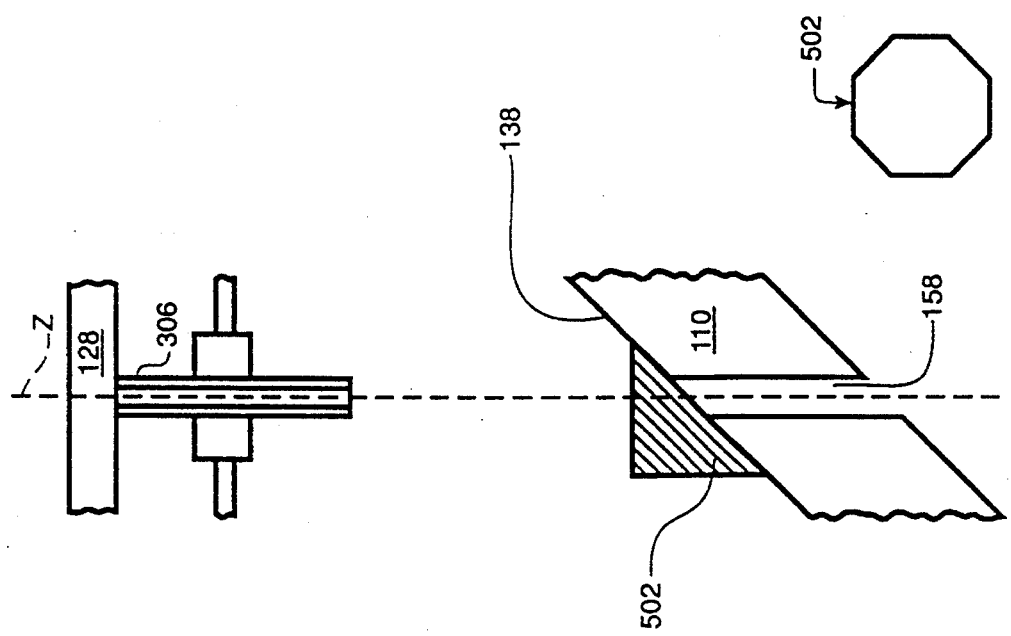

5,460,045

ULTRASONIC PROBES FOR INSPECTION OF REACTOR PRESSURE VESSEL BOTTOM HEAD AND WELD BUILDUP THEREON

This application is a divisional application of U.S. patent application Ser. No. 07/865,507 filed on Apr. 9, 1992, which issued as U.S. Pat. No. 5,272,734 on Dec. 21, 1993.

BACKGROUND OF THE INVENTION

The present invention relates to nuclear reactors and, more particularly, to a method of repairing a boiling-water nuclear reactor.

Nuclear reactors are conservatively specified to minimize any risks from the hazardous materials involved in their use. Reactor vessel walls are several inches thick and the strongest materials are used for reactor components. Nonetheless, contingencies are required for failure as components are subjected to extreme stress for decades. These contingencies involve not only many layers of preventive systems, but also procedures for rectifying problems that arise.

Of concern herein are incore-housing-related defects. Incore instrumentation housings, referred to more simply as "incore housings", house the links between instrumentation used to monitor the core and the host system used to analyze the data collected by instrumentation. The housings are tubular and penetrate the reactor vessel bottom, to which they are welded. Incore-housing-related defects include defects in the housing itself, in the weld bonding the housing to the vessel bottom and in the vessel bottom in the vicinity of the housing. These defects can cause or lead to leaks from the reactor vessel. Accordingly, a method is required to address such defects.

Drastic approaches involve long-term shutdown of the reactor. The reactor could be replaced or removed, repaired, and reinstalled. These approaches are extremely costly, and alternatives are highly desirable. Some incore housing defects can be addressed by inserting a sleeve onto the incore housing to cover the defects and stop whatever leaking might occur. However, such patch approaches do not really address the defect, which can continue to grow due to further fatiguing. Furthermore, the weld between the sleeve and the housing can be a new source of defects.

More recently, a method has been developed for replacing an incore housing that minimally impacts reactor components other than those being replaced. This method involves removal of all fuel from the reactor and performing most steps under water to minimize radiation exposure. While providing a relatively permanent repair and while being relatively economical, this method involves a series of over 100 procedures, several of which could introduce new defects. Such defects may be serious enough to force repetition of the replacement method. This repetition is undesirably time consuming and expensive. What is needed is an improved method of effecting a relatively permanent repair of an incore housing defect that is relatively economical and, preferably, minimally disruptive of the reactor system.

SUMMARY OF THE INVENTION

In accordance with the present invention, an improved method for replacing an incore housing includes an integral series of ultrasonic inspections. The ultrasonic inspections minimize the amount of re-repairing required in case the repair procedure introduces a defect. Also in accordance with the present invention, most of the steps, including the ultrasonic inspections, are done underwater to minimize radiation exposure.

There are three major stages to the method, each having a major structural objective and an associated ultrasonic inspection. The first stage involves removal of the original housing and inspection of remaining weld material and exposed cladding at the reactor vessel bottom. The second stage involves forming a weld buildup and ultrasonically inspecting the weld buildup. The third stage involves welding a new housing to the weld buildup and ultrasonically inspecting the new housing and its attachment to the weld buildup.

The method begins with the removal of the original incore housing. Initially, all fuel is removed from the reactor, leaving a vacated core region. The reactor vessel remains filled to its normal level with water. An ultrasonic scanner with a first ultrasonic probe is installed over the aperture through which the incore housing penetrated the reactor bottom. The scanner is installed beneath the core region in the space vacated by the removed housing.

The attached first probe has a disk-shaped probe head that is free to tilt relative to the vertical shaft between it and the scanner. When the probe head is lowered to contact the reactor bottom, the probe head orientation conforms to the local contour of the bottom. An ultrasonic examination of cladding on the reactor bottom, and of unremoved weld material, is conducted while rotating the disk-shaped probe head about the shaft axis. The probe head continuously reorients as required to maintain conformity with the local contour of the bottom. The scanner and the first probe are removed from the reactor vessel. If no defects are found, or if detected defects are appropriately corrected, the procedure continues as follows.

Water is removed from the vessel. A weld buildup is formed over the aperture. The vessel is refilled with water, submerging the core region. In addition, the exterior of the weld buildup is machined smooth to aid in subsequent ultrasonic inspection. An aperture is machined through the weld buildup to provide access through the original bottom aperture.

Once the weld buildup is finished, a second ultrasonic probe is attached to the scanner; the scanner is secured in the space vacated by the removed incore housing. The head of the second probe has a relatively large diameter so that it fills most of the aperture through the weld buildup, except for an annular portion next to the inner wall of the weld buildup. The probe head is scanned vertically along the weld buildup aperture to inspect the weld buildup for defects. Between vertical scans, the head is stepped circumferentially in appropriate, e.g., 2°–6°, increments. The increments are chosen to ensure overlap of successive scans so that no inspection volume is skipped. Thus, a cylindrical raster scan of the weld buildup is performed. The scanner and attached second probe are removed from the reactor. Once again, if no defects are found, or if detected defects are appropriately corrected, the procedure continues.

An annular groove having a "J"-shaped cross section is machined in the top of the weld buildup adjacent to the buildup aperture. This "J-prep" is in preparation for the weld between the weld buildup and a replacement incore housing. This replacement incore housing is inserted up through the vessel bottom. The new housing extends only several inches above the bottom contour of the vessel. Once the replacement incore housing is installed, water is removed from the reactor and the housing is "J-welded" to the weld buildup at the J-prep. The reactor is refilled.

A third probe is attached to the scanner, and the scanner with third probe attached is secured just above the inserted housing. The head of this third probe is a relatively small diameter cylinder so that it fits with clearance through the interior of the replacement housing. This third head is lowered into the housing and a cylindrical raster scan of the housing and J-weld is performed. The scanner with third probe attached is removed. If no defects are detected or if detected defects are corrected, no more ultrasonic testing is required. A shrink coupling assembly is attached to the replacement housing and to the associated incore guide tube. Steam is applied to secure the shrink coupling. Repair is essentially complete.

While the resulting structure differs from the original by the presence of the shrink coupling, it is essentially "like new" where the housing is attached to the weld buildup and the vessel bottom. This repair is effected without disruption of nearby components, and the reactor can be returned to operation with minimum delay. The repair is more permanent than various patches, and more economical and convenient than radical approaches that require major reactor disassembly. These and other features and advantages of the present invention are apparent from the description below with reference to the following drawings.

BRIEF DESCRIPTION OF THE DRAWINGS

FIG. 5A is a schematic elevational view of the reactor portion of FIG. 3B, but after a solid weld buildup has been formed.

FIG. 5B is a plan view of the solid weld buildup of FIG. 5A.

FIG. 5C is a schematic elevational view of the reactor portion of FIG. 5A, but after the weld buildup of FIG. 5A has been machined, yielding an apertured weld buildup.

FIG. 5D is a plan view of the apertured weld buildup of FIG. 5C.

DESCRIPTION OF THE PREFERRED EMBODIMENTS

Figure 1:
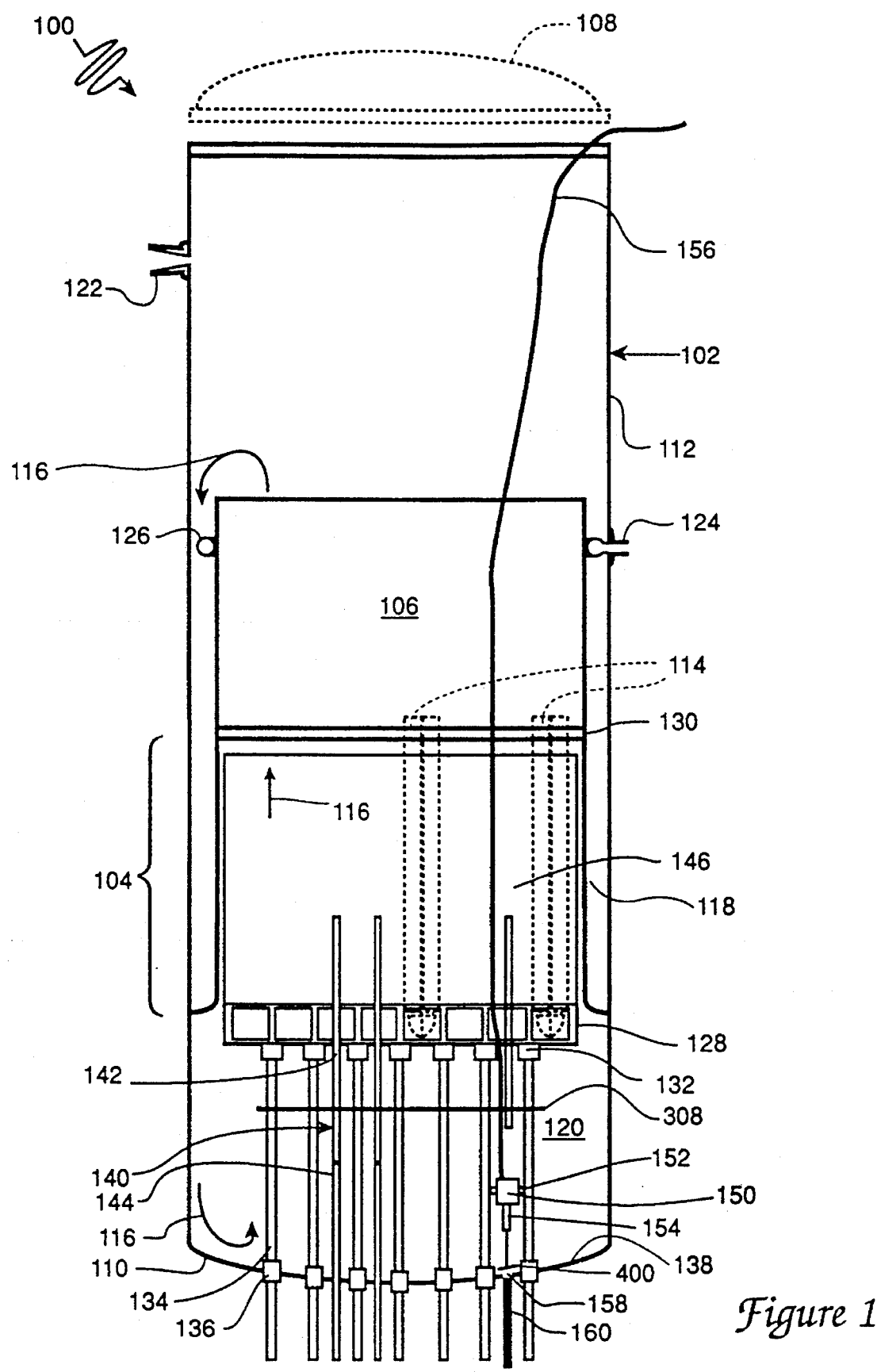
FIG. 1 is a schematic elevational view of a reactor on which a method in accordance with the present invention is practiced.

A boiling-water nuclear reactor 100 is shown in the process of repair in FIG. 1 according to a method of the present invention. Reactor 100 comprises a reactor vessel 102, a reactor core region 104, and a shroud 106, as shown in FIG. 1. Vessel 102 comprises a top head 108, a bottom head 110, and a cylindrical sidewall 112. During reactor operation, core region 104 comprises an array of vertically extending fuel bundles 114. (Fuel bundles 114 and top head 108 are shown in phantom because they are removed at the time represented in FIG. 1.)

When the reactor is in operation, water circulates (as shown by arrows 116) up through core region 104, radially outward to an annular downcomer 118, down to a lower plenum 120, and up again through core region 104. Some of the water rising through core region 104 is converted to steam by heat released as fissile fuel in bundles 114 fissions. Steam exits vessel 102 through a steam exit nozzle 122, whence it is directed to a turbine that drives an electric generator. In giving up energy to the turbine, the steam condenses, and the condensate returns to vessel 102 via a feedwater nozzle 124 for distribution about downcomer 118 via a feedwater sparger 126.

Fuel bundles 114 are guided by a core plate 128 and held in place from above by a top guide 130. Core power is regulated by inserting and retracting control rods that slide vertically within control rod guide tubes 132, driven by control rod drives housed within control rod drive (CRD) housings 134. CRD housings 134 are welded to stub tubes 136, which are in turn welded in corresponding apertures through bottom head 110 of vessel 102. Bottom head 110 has a cladding 138 on its interior surface.

Core power is monitored by neutron flux monitors, located within incore housing assemblies 140. Each incore housing assembly 140 includes an instrumentation guide tube 142 and an incore housing 144. Each incore housing 144 extends through bottom head 110 to abut the corresponding instrumentation guide tube 142, to which it is welded. Incore monitoring instruments are inserted into reactor 100 from below and through incore housings 144. Motion of the instrumentation within core region 104 is guided vertically by instrumentation guide tubes 142. The division of incore housing assemblies 140 into guide tubes 142 and housings 144 simplifies reactor manufacturing. In the alternative, a monolithic tube can serve as both the incore housing and the instrumentation guide tube.

In the repair in progress represented in FIG. 1, an inspection of welds in cladded vessel bottom head 110 has identified an incore-housing-related defect requiting repair. Vessel top head 108 has been removed from vessel sidewall 112; all fuel bundles 114 have been removed from core region 104. This defines an access 146 through core region 104 through which a scanner 150 and other repair equipment can be inserted into lower plenum 120.

Scanner 150 is braced against adjacent CRD housings 134 using brackets 152. Scanner 150 includes a scanner shaft 154 with a bayonet mount to which probes can be attached. A cable 156 provides power and control commands to scanner 150 and provides for transmission of data from scanner 150 to an external host computer system. Scanner 150 has a short coaxial cable (not shown) that connects to a like cable attached to the interchangeable probes to permit communication therebetween.

Portions of the indicated incore housing assembly have been removed to allow the inspection of the vessel bottom head and the welds attaching the incore housing to the vessel bottom head. An aperture 158 has been exposed in vessel bottom head 110. A new incore housing is to be inserted through aperture 158 and welded in place to effect repair of the indicated incore housing assembly. At the step represented in FIG. 1, aperture 158 is plugged with a mandrel 160 to prevent water from escaping from vessel 102.

Figure 2:
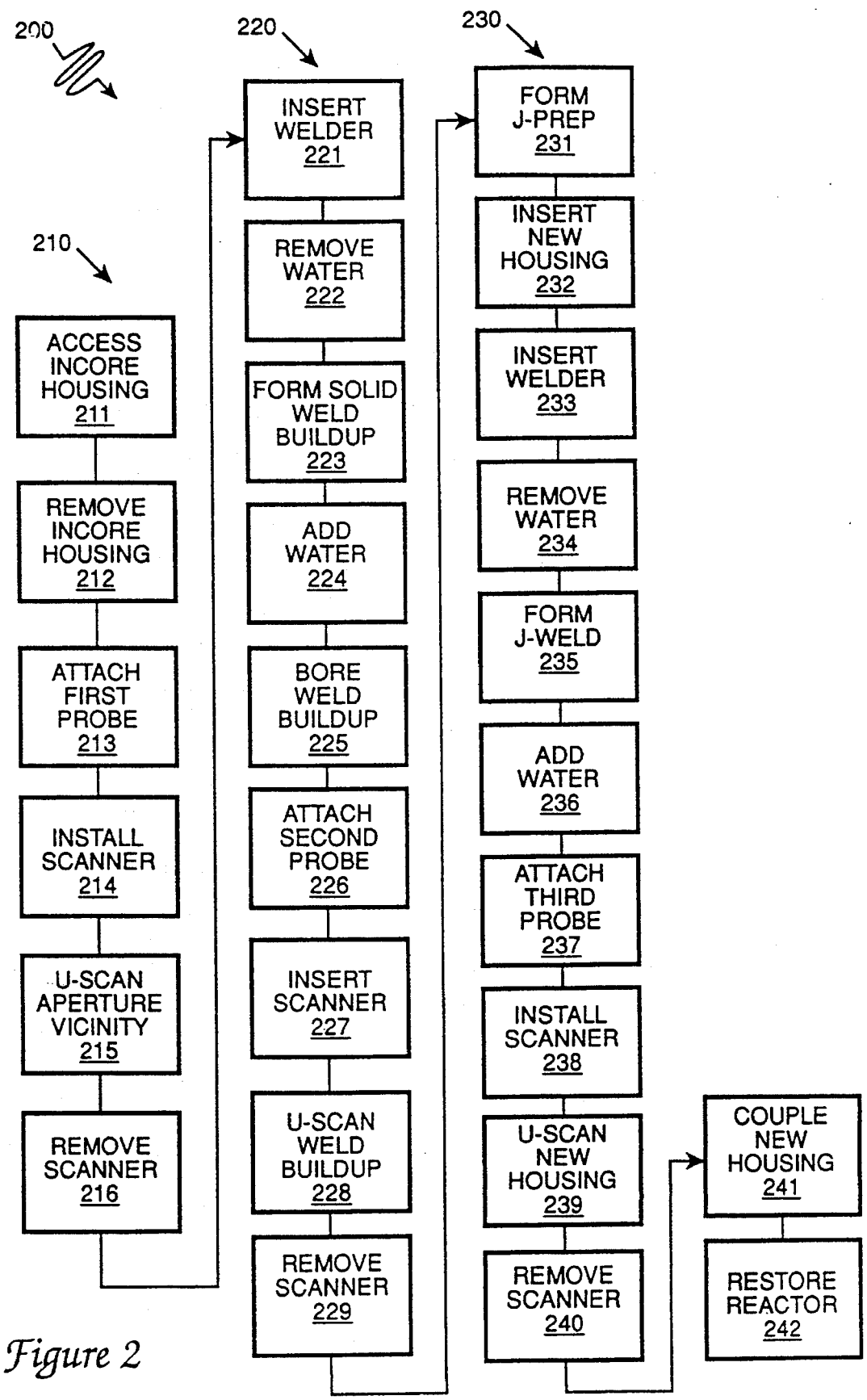
FIG. 2 is a flow chart of a method in accordance with the present invention.

The method 200 of the present invention, effecting the repair shown in progress in FIG. 1, is flow charted in FIG. 2. Method 200 addresses a repair (such as that represented in FIG. 1) of defects in an incore housing 144, defects in the weld material bonding the incore housing to bottom head 110, and defects in the local bottom head cladding. Method 200 comprises three stages: a first stage 210 involving removal of an indicated incore housing and inspection of a weld area of bottom head 110; a second stage 220 involving weld buildup and inspection thereof; and a third stage 230 involving insertion and welding of a new incore housing and inspection of the attaching weld.

First stage 210 begins with gaining access, at step 211, to an incore housing indicated for repair. To gain access, reactor 100 is shut down and vessel top head 108 is separated from vessel 102. All fuel bundles 114 are removed, providing an access 146. Various other components (not shown) such as a steam separator and a steam dryer are also removed to provide access to lower plenum 120 below core region 104.

Figure 3B:
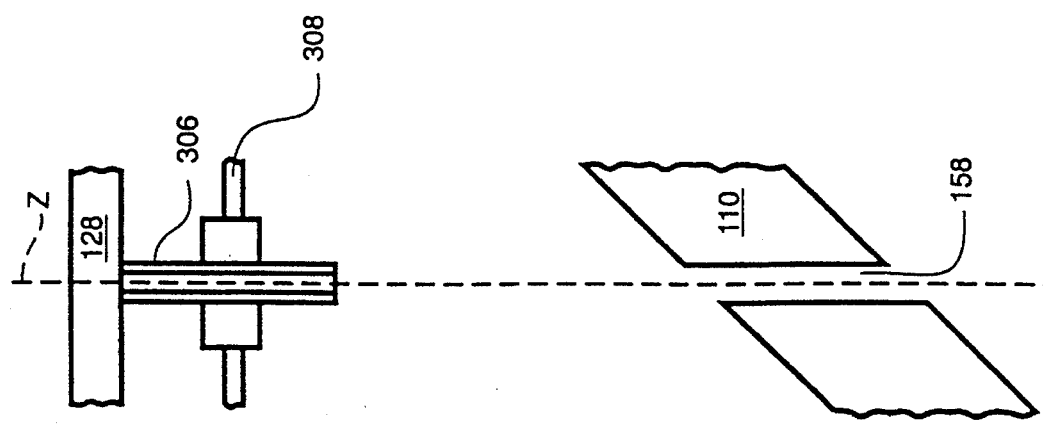
FIG. 3B is a schematic elevational view of the portion of the reactor shown in FIG. 3A, but after the indicated incore housing has been removed.
Figure 3A:
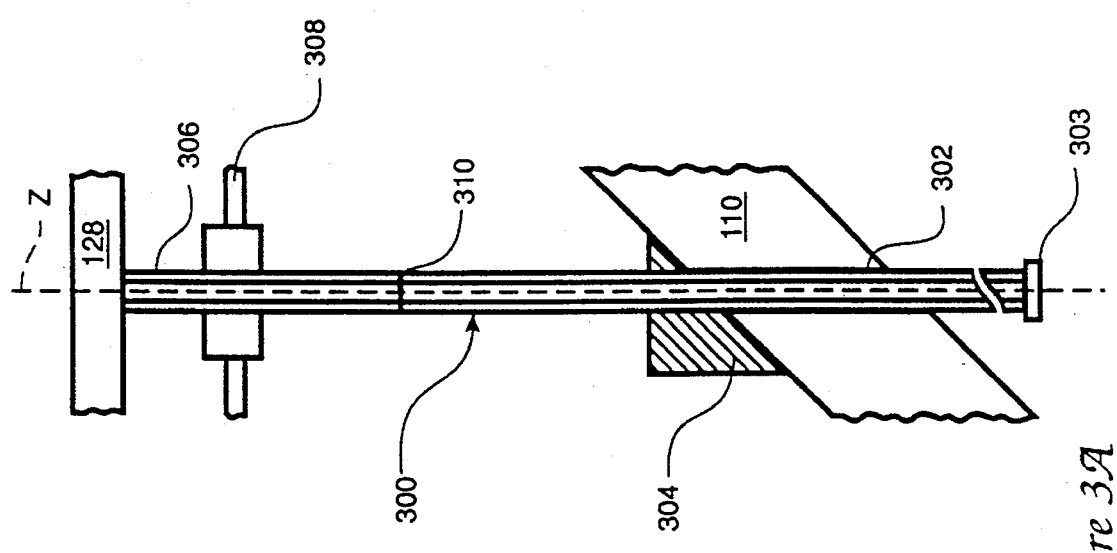
FIG. 3A is a schematic elevational view of a portion of the reactor of FIG. 1 illustrating an indicated incore housing to be replaced.

At step 212, a portion of an indicated incore housing assembly 300, shown in FIG. 3A, is removed. Prior to this removal, the included incore housing 302 is sealed by flange 303 from below. An electrical discharge machine (EDM) is inserted into lower plenum 120 down through core region 104, and is used to make cuts through incore housing assembly 300 to detach portions of the incore housing above an original weld buildup 304. A lower portion of the attached incore guide tube 306 below attached stabilizer bars 308 is also removed. This process necessarily removes a weld 310 between incore guide tube 306 and incore housing 302. The EDM machine is also used to remove most of weld buildup 304, exposing aperture 158 in bottom head 110, as seen in FIG. 3B. Exposed aperture 158 is sealed from above, and the remaining portion of incore housing 302 is removed from below vessel 102. Mandrel 160, shown in FIG. 1, is inserted from below into aperture 158, allowing the seal above aperture 158 to be removed while maintaining water within vessel 102.

Figure 4A:
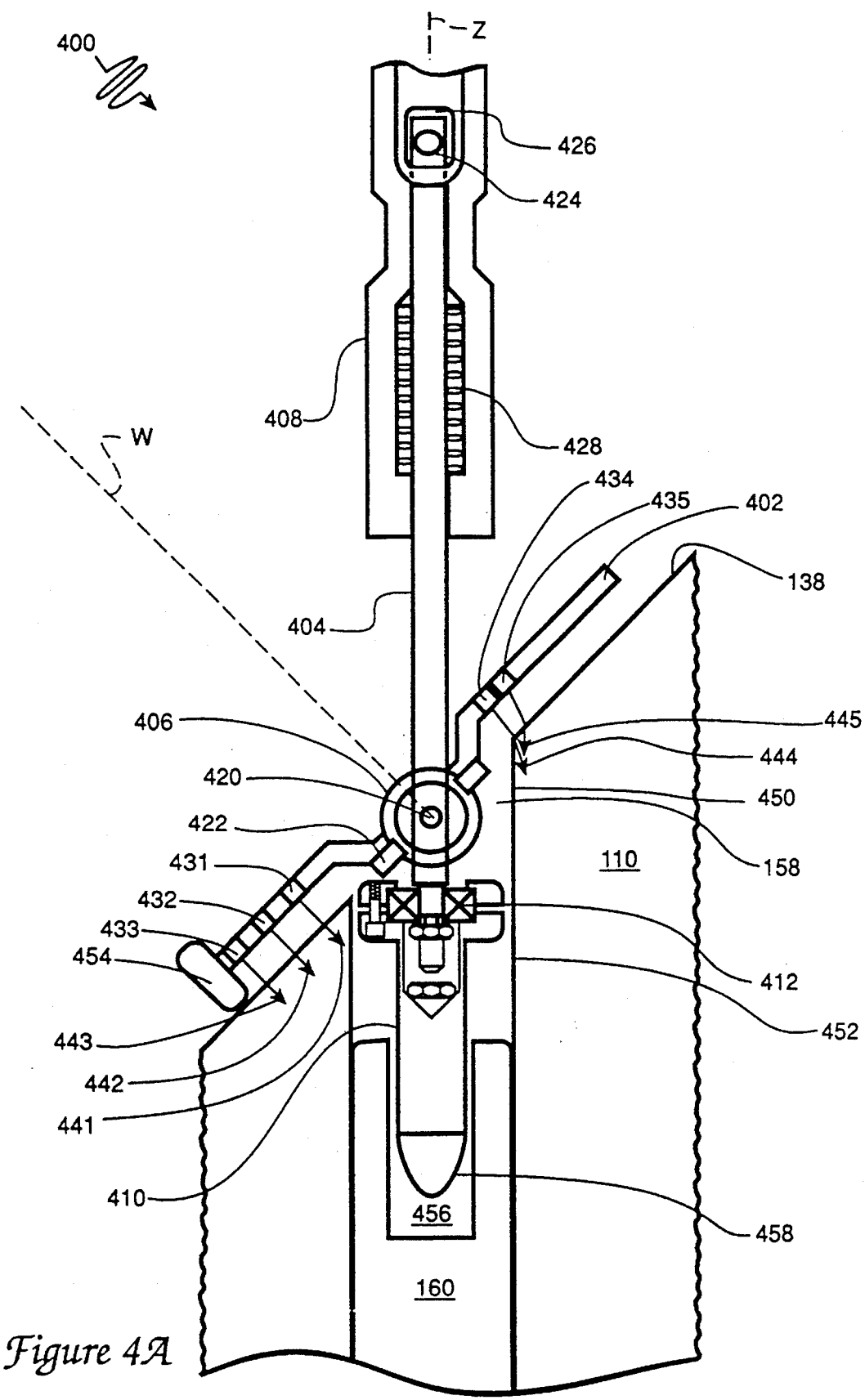
FIG. 4A is an elevational view of a first ultrasonic probe used in the method of FIG. 2, showing beam patterns of its transducers.

At step 213, a first probe 400, shown in FIG. 4A, is attached to scanner shaft 154. At step 214, scanner 150 with first probe 400 attached is installed in lower plenum 120 in the space vacated by removed incore housing 302. Scanner 150 is aligned so that its shaft 154 extends along a Z-axis, represented in FIG. 3A, of aperture 158. Scanner 150 is basically cylindrical, with a diameter small enough that it can be delivered into lower plenum 120. Brackets 152 position scanner 150 between adjacent control rod drive housings 134. Scanner 150 effects external communication through cable 156, which extends up through core region 104 and out of vessel 102. Reactor 100 is shown at the completion of step 214 in FIG. 1.

First probe 400 is used in a first ultrasonic scan (U-scan) of the surfaces and volume that will underlie the weld buildup to be formed in the second stage 220 of method 200. Accordingly, any remaining weld buildup, the wall of aperture 158, the local cladding, and the adjacent bottom head volume are ultrasonically interrogated.

First probe 400 has a disk-shaped head 402 (see FIG. 4B) that is tiltably coupled to a lower shaft 404 via a coupling ball 406. Lower shaft 404 is coupled to an upper shaft 408, which is in turn bayoneted to scanner shaft 154. A centering member 410 is coupled to the bottom of lower shaft 404 via a ball bearing assembly 412, permitting free relative rotation of lower shaft 404 and centering member 410. Probe 400 also has a coaxial cable (not shown) that mates with the coaxial cable of scanner 150 to permit communication therebetween.

Figure 4B:
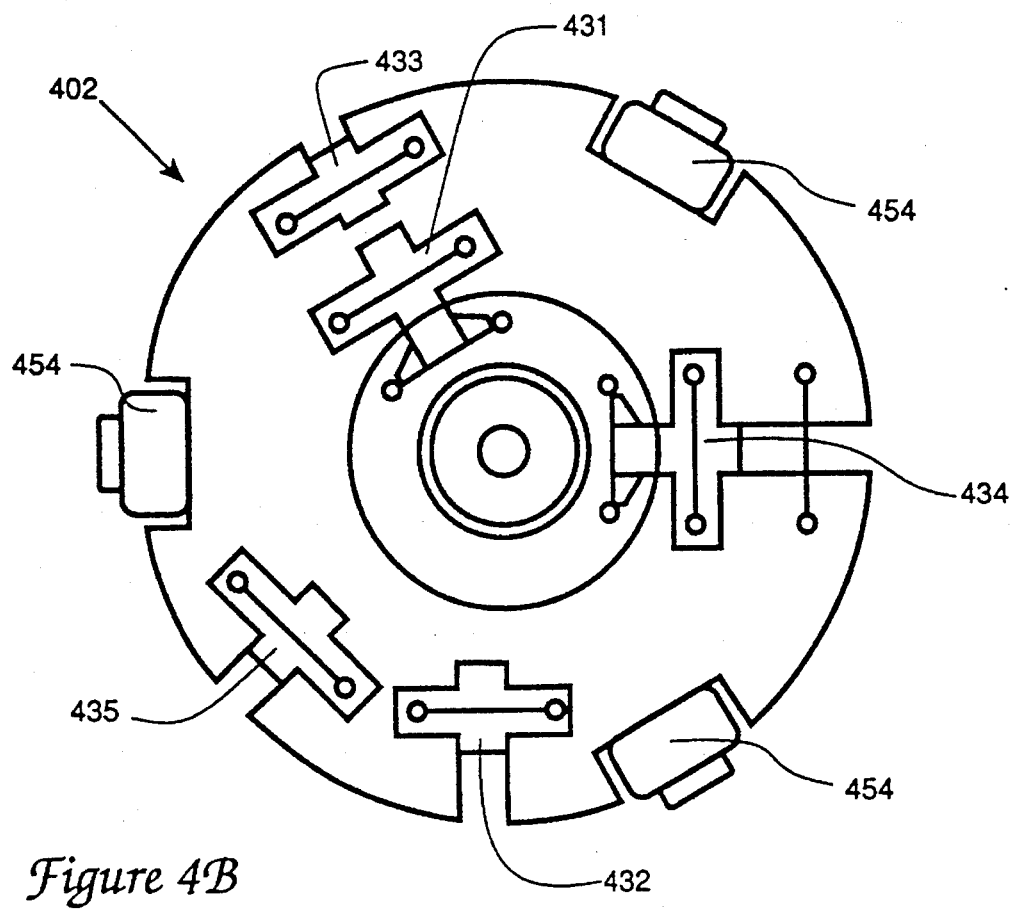
FIG. 4B is a bottom plan view of a disk head of the probe of FIG. 4A showing its arrangement of transducers.
Figure 4C:
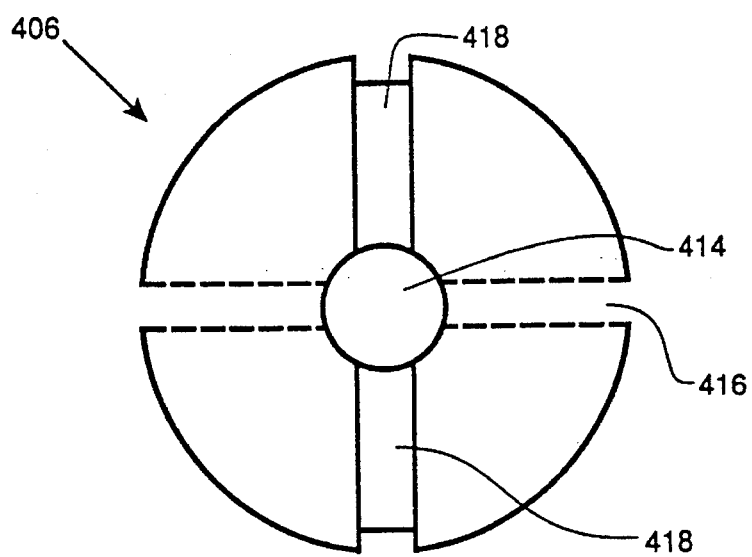
FIG. 4C is a schematic plan view of a ball used to mechanically couple components of the probe of FIG. 4A.

Coupling ball 406 is spherical and includes a vertical hole 414, a transverse hole 416, and an annular groove 418, as shown in FIG. 4C. Lower shaft 404 extends through vertical hole 414; a pin 420 through transverse hole 416 and lower shaft 404 prevents relative rotation of coupling ball 406 and lower shaft 404, as indicated in FIG. 4A. Thus, for practical purposes, coupling ball 406 is rigidly coupled to lower shaft 404. Annular groove 418 is a great circle through both ends of vertical hole 414. Disk-shaped head 402 has a pair of pins 422 that engage groove 418, as seen in FIG. 4A. This arrangement allows disk-shaped head 402 to tilt about groove 418 and relative to lower shaft 404. Thus, when lowered to press against bottom head 110, disk-shaped head 402 can tilt to conform to the local contour of bottom head 110.

Lower shaft 404 fits within upper shaft 408. An outwardly extending pin 424 of lower shaft 404 extends through a vertically elongated hole 426 of upper shaft 408, as indicated in FIG. 4A. This arrangement prevents relative rotation and limits relative vertical motion of shafts 404 and 408. A spring 428 in the space between lower shaft 404 and upper shaft 408 urges the shafts apart to the extent permitted by pin 424 and hole 426, and forces probe 400 toward cladding 138.

Scanning involves rotating scanner shaft 154, and thus disk-shaped probe head 402, via the linkage provided by shafts 404 and 408. Disk-shaped head 402 has five transducers 431–435 directed generally downward which scan, at step 215, the surfaces and volume adjacent to aperture 158.

Transducers 431–435 of disk-shaped head 402 include inner, intermediate, and peripheral straight-beam transducers 431, 432, and 433, respectively, and medium-angle and high-angle transducers 434 and 435, respectively, as shown in FIGS. 4A and 4B. A coaxial cable from probe 400 mates with the coaxial cable of scanner 150 to provide for bi-directional communication between transducers 431–435 and scanner 150. Straight-beam transducers 431, 432, and 433 direct respective beams 441, 442, and 443 perpendicular to disk head 402, as shown in FIG. 4A. Since disk head 402 is parallel to the adjacent cladding 138 on the interior surface of bottom head 110, these beams are not bent by refraction. Thus, they penetrate straight into cladding 138 and bottom head 110.

At positions away from the center of bottom head 110, the three straight-beam transducers 431–433 can fail to interrogate regions critical to a thorough inspection. For example, they do not effectively interrogate the high-side 450 of wall 452 of aperture 158. Accordingly, angled beam transducers 434 and 435 are designed to interrogate regions missed by the straight beams.

High-angle transducer 435 directs its refracted-longitudinal beam 445 46° from the perpendicular and toward the center axis W of disk-shaped head 402, as shown in FIG. 4A. The 46° corresponds roughly to the maximum slope in the vicinity of any of the incore housings. Thus, when a peripheral incore housing is being replaced, high-angle transducer 435 directs its beam 445 parallel to high-side 450 of aperture wall 452.

Medium-angle transducer 434 directs its refracted-longitudinal beam 444 20° from the perpendicular toward the W axis. Medium-angle transducer 434 interrogates regions missed by the extremes of straight-beam transducers 431–433 and high-angle transducer 435.

Three rollers 454 are mounted on disk-shaped head 402, as shown in FIG. 4B. The action of spring 428 forces rollers 454 into intimate contact with cladding 138. Rollers 454 maintain a proper spacing of transducers 431–435 from vessel bottom 110 to minimize noise due to spurious reflections. In addition, rollers 454 facilitate a rotation of disk-shaped head 402 during scanning. Scanning involves one 360° rotation of disk-shaped head 402.

In operation, commands are received by scanner 150 via cable 156. Scanner 150 then lowers first probe 400 so that centering member 410 enters bottom head aperture 158 and then a hole 456 of mandrel 160. The insertion is facilitated by tapered end 458 of centering member 410. Little clearance is provided for centering member 410. If rotation of centering member 410 is constrained by particles lodged between it and mandrel 160, ball bearing assembly 412 permits the rest of first probe 400 to rotate without this constraint.

Scanner 150 lowers first probe 400 until rollers 454 contact cladding 138 with sufficient force to compress spring 428, as indicated by the upward movement of pin 424 relative to hole 426 of upper shaft 408. Transducers 431–435 are activated as appropriate, and scanner 150 causes disk-shaped head 402 to rotate stepwise through 360° in preselected increments; the increments are preferably between 2° and 6° inclusive. In the illustrated embodiment, 4° increments were employed. Ultrasonic reflections are gathered by the transducers and the resulting defect data is communicated to the remote host system via cable 156. Scanner 150 and first probe 400 are removed after inspection, at step 216.

If defects are found in the remaining weld material, further machining can remove the defective material. Defects in the cladding on which further weld material is to be formed can be addressed on a case-by-case basis. A follow-up inspection can be used to evaluate the correction. If no defects are found, or once detected defects are corrected, the first stage 210 of method 200 is completed, and second stage 220 can proceed.

Second stage 220 begins with the insertion, at step 221, of welding equipment into lower plenum 120. Top head 108 is put in place, leaving a gap sufficient for control cabling of the welding equipment. Vessel 102 is drained at step 222. The welding equipment is then used to form, at step 223, a solid weld buildup 502, as shown in FIG. 5A, over the previously inspected cladding 138 and aperture 158. Vessel 102 is refilled with water, at step 224, and top head 108 is removed. The welding equipment can be removed at this point.

Due to the motion control system of the welding equipment, weld buildup 502 is in the shape of a solid octagonal prism, as indicated in FIG. 5B. The EDM machine is inserted, at step 225, to smooth the exterior of weld buildup 502 and to bore an aperture 504 therethrough, resulting in apertured weld buildup 506, illustrated in FIGS. 5C and 5D. Aperture 504 is required to admit a new incore housing. Smoothing the rough octagonal exterior to a smooth cylindrical exterior 508, as indicated in FIG. 5D, improves the inspectability of apertured weld buildup 506.

Figure 6A:
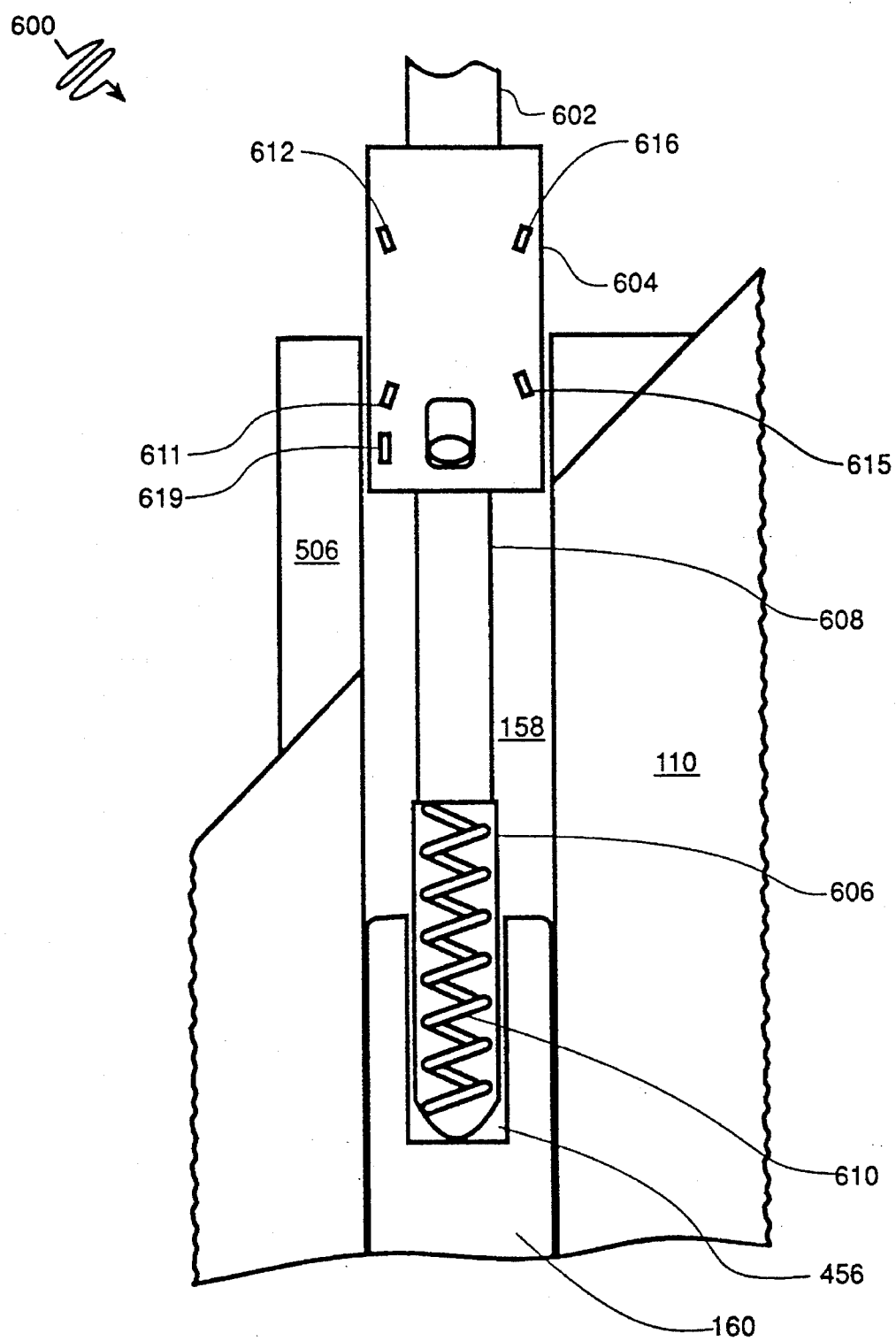
FIG. 6A is a schematic elevational view of a second probe (in an uncompressed state) used in the method of FIG. 2.

A second probe 600, as shown in FIG. 6A, is attached to scanner 150, at step 226. Second probe 600 comprises a probe shaft 602, a probe body 604, and a centering member 606, as shown in FIG. 6A. Probe body 604 has a downwardly extending projection 608. Projection 608 fits within and can move vertically relative to centering member 606. A spring 610 mounted within centering member 606 urges probe body 604 upward, to maximum separation.

Figure 6B:
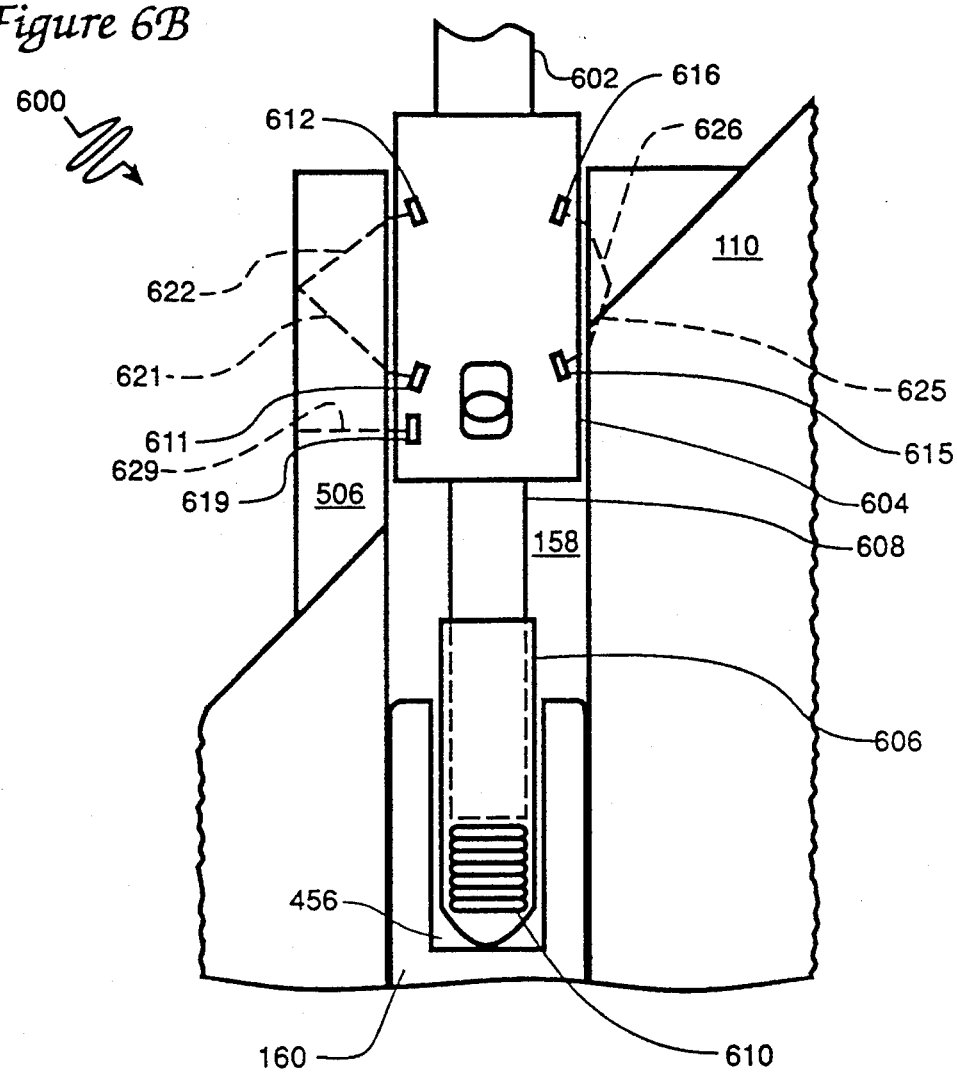
FIG. 6B is a schematic elevational view of the second probe of FIG. 6A in a compressed state.
Figure 6C:
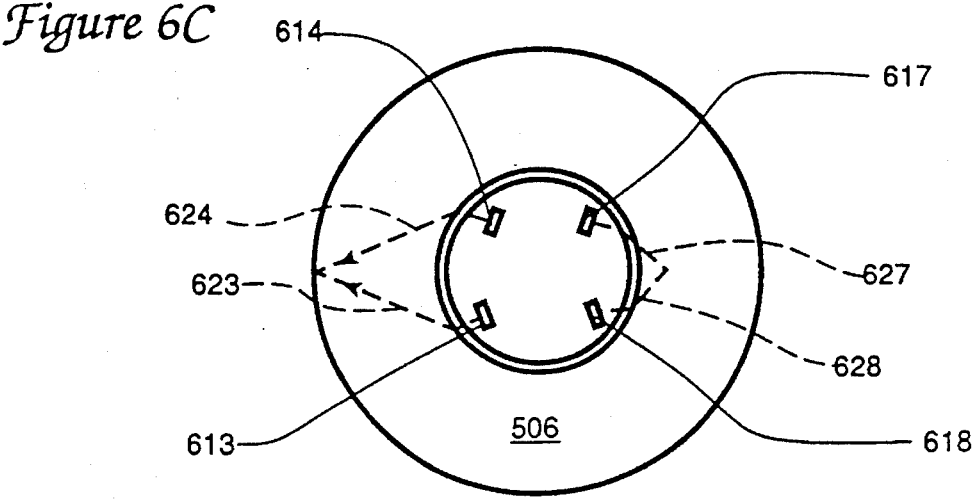
FIG. 6C is a schematic plan view showing beam patterns of the second probe of FIG. 6A.

Probe body 604 has nine transducers 611–619 for producing ultrasound beams 621–629, as indicated in FIGS. 6B and 6C. Transducer 619 is oriented so that its beam 629 is directed radially outward into weld buildup 506, as shown in FIG. 6B. Transducers 611–618 are arranged in two groups of four. The groups are disposed in recesses on opposite sides of probe body 604.

The first group contains four transducers 611–614 targeted to the outer diameter of weld buildup 506. Transducer 611 is oriented so that its beam 621 is directed upward, and transducer 612 is oriented so that its beam 622 is directed downward, as shown in FIG. 6B. Transducer 613 is oriented so that its beam 623 is directed clockwise, and transducer 614 is oriented so that its beam 624 is directed counterclockwise, as shown in FIG. 6C.

The second group contains four transducers 615–618, all targeted at the inner diameter of weld buildup 506. Transducer 615 is oriented so that its beam 625 is directed upward, and transducer 616 is oriented so that its beam 626 is directed downward, as indicated in FIG. 6B. Transducer 617 is oriented so that its beam 627 is directed clockwise, and transducer 618 is oriented so that its beam 628 is directed counterclockwise, as indicated in FIG. 6C.

In operation, probe shaft 602 is bayoneted to scanner shaft 154. A coaxial cable (not shown) of probe 600 is connected to the respective coaxial cable of scanner 150 and provides for bidirectional communication between probe transducers 611–619 and scanner 150. Scanner 150 with probe 600 attached is installed in the same location below core region 104 and over aperture 158, at step 227.

Scanner 150 lowers second probe 600 until the bottom of centering member 606 contacts the base of hole 456 in mandrel 160. Initially, transducers 611–619 are at or above the top of weld buildup 506. Transducers 611–619 are activated, producing beams 621–629. Scanner 150 drives probe 600 vertically downward, compressing spring 610 and thus lowering probe 600 as indicated in FIG. 6B. When the transducers reach the base of weld buildup 506, scanner 150 rotates the probe 4°, and probe body 604 scans upward. Scanning continues with vertical sweeps separated by rotations. In step 228, this raster motion is continued for 360° of rotation. Scanner 150 and second probe 600 are then lifted and removed, at step 229. Detected defects require repair of weld buildup, or removal and formation of a new weld buildup. If no defect is detected, or once detected defects are corrected, second stage 220 is completed.

Figure 7B:
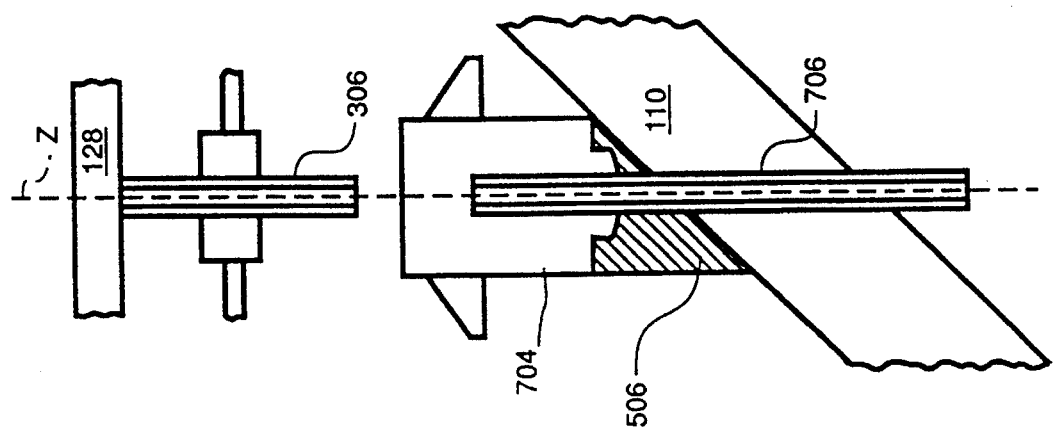
FIG. 7B is a schematic elevational view of the reactor portion of FIG. 7A, but after a replacement incore housing has been inserted through the weld buildup.
Figure 7A:
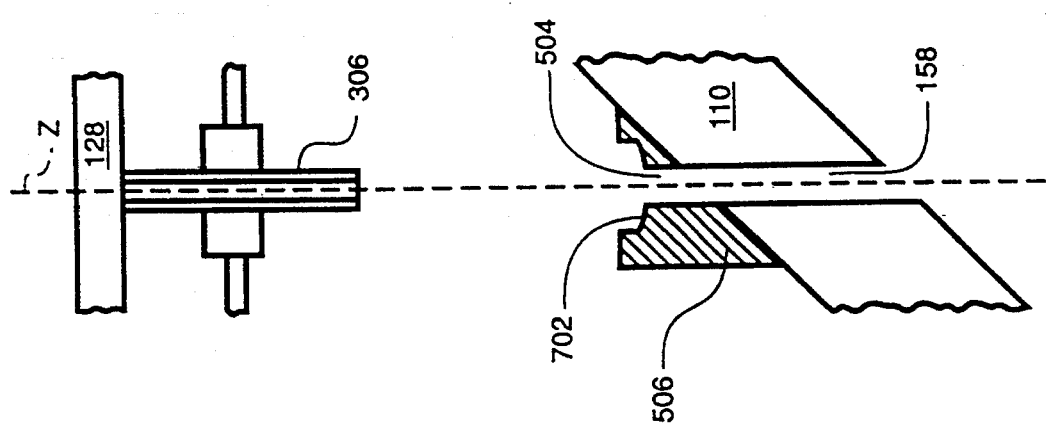
FIG. 7A is a schematic elevational view of the reactor portion of FIG. 5C, but after a J-prep has been machined in the weld buildup.

In third stage 230, the EDM machine is inserted again to form, at step 231, a J-preparation 702 in weld buildup 506. J-prep 702 is an annular groove with a J-shaped cross-section, as shown in FIG. 7A. The EDM equipment is then removed. A "top hat seal" 704, shown in FIG. 7B, is placed over aperture 504. Top hat seal 704, so named for its shape, provides clearance for the insertion of a new incore housing 706 while maintaining water in vessel 102.

Mandrel 160 is removed and a hydroswage is inserted into new incore housing 706, which is installed at step 232. Unlike removed incore housing 302 that extended to incore guide tube 306, new incore housing 706 extends only about 6" above new weld buildup 506. The 6" clearance is provided by top hat seal 704.

The hydroswage is pumped up, causing incore housing 706 to bulge at the level of and seal against bottom head 110. This seal prevents water from leaking out of vessel 102 between bottom head 110 and incore housing 706 once top hat seal 704 is removed. The hydroswage is removed and the bottom of incore housing 706 is sealed to prevent water escaping vessel 102 through the interior of incore housing 706.

Figure 8A:
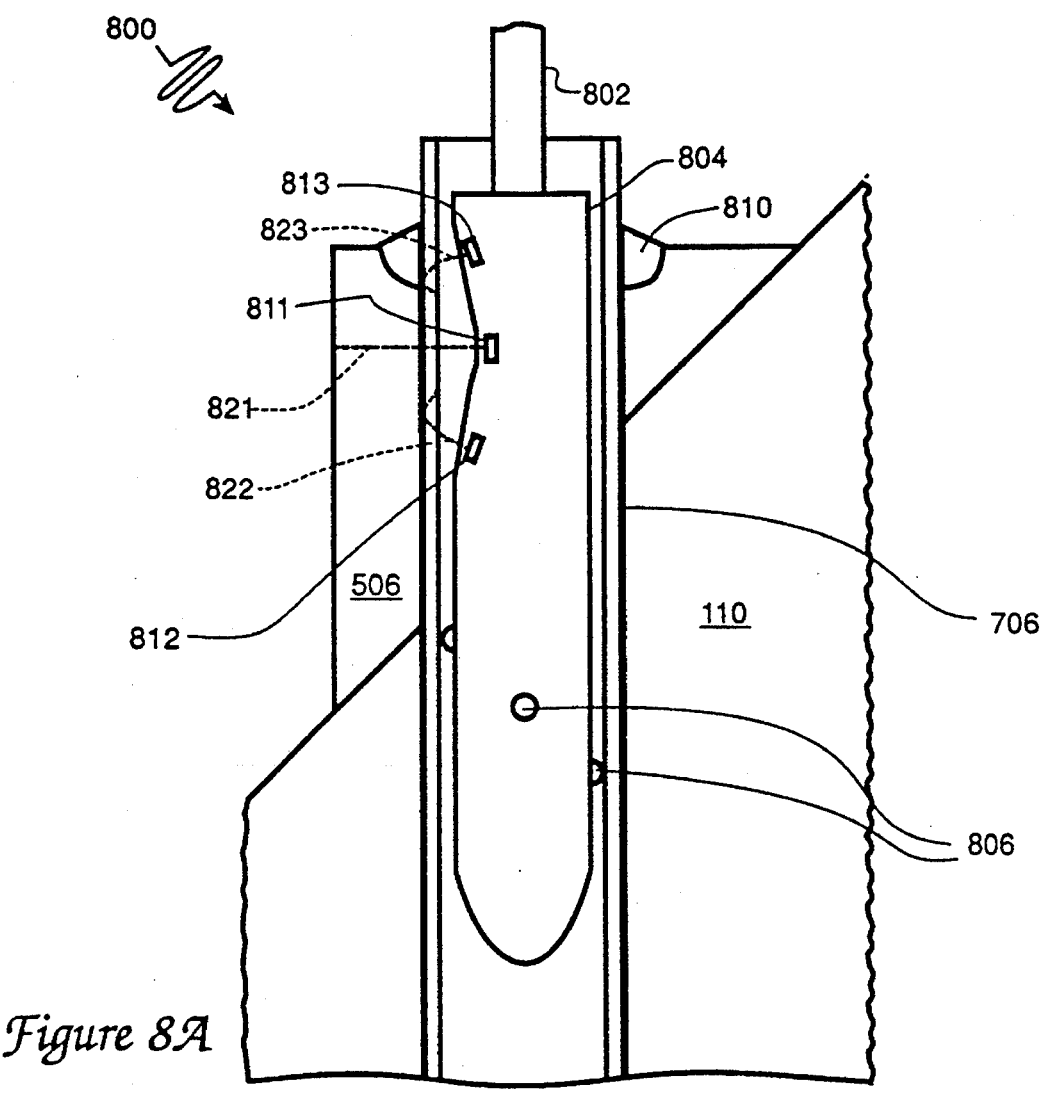
FIG. 8A is a schematic elevational view of a third probe used in the method of FIG. 2.
Figure 9:
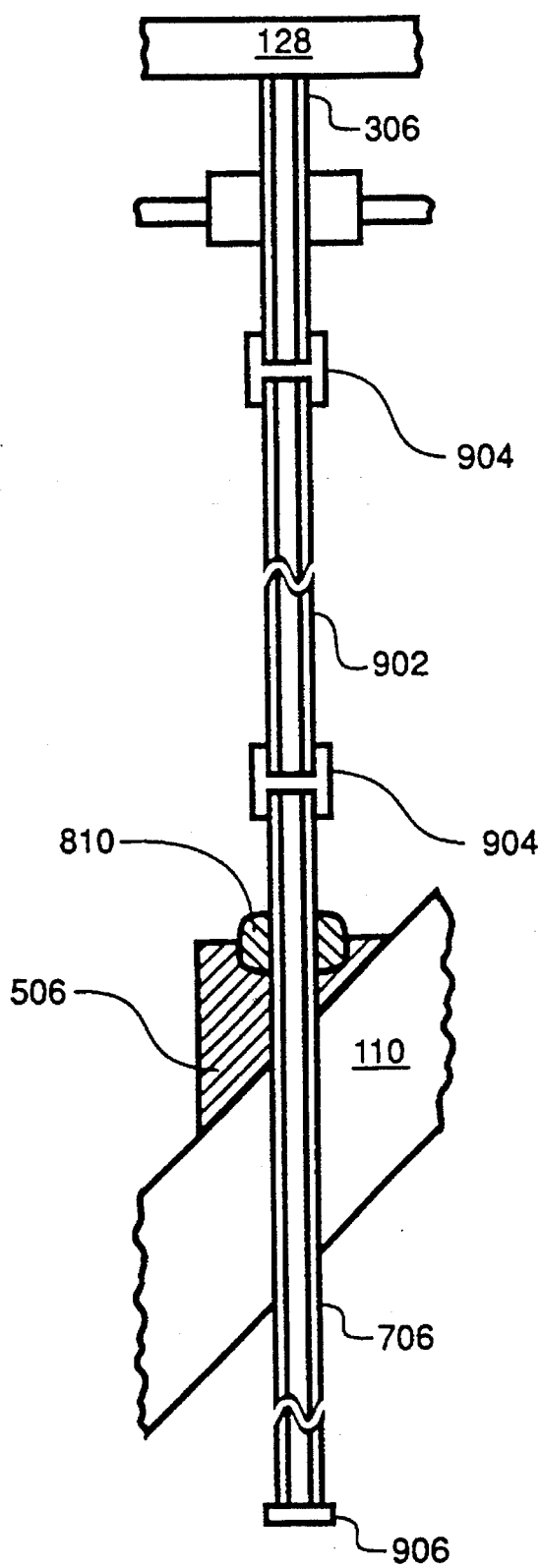
FIG. 9 is a schematic elevational view of the reactor portion of FIG. 7B, but after a J-weld has been formed and after a tube coupling has been installed.

Welding equipment is then inserted, at step 233, into vessel 102. Top head 108 is placed on vessel 102. Water is drained from vessel 102, at step 234. Top hat seal 704 is removed. A J-weld 810, as shown in FIG. 8A, is formed, at step 235. The seal at the bottom of incore housing 706 is removed. A flange 906, see FIG. 9, is attached to new incore housing 706, sealing the vessel interior. Vessel 102 is refilled with water, at step 236. Top head 108 and the welding equipment are removed.

A third probe 800 with a shaft 802 and a cylindrical probe head 804 with a tapered bottom, shown in FIG. 8A, is attached to scanner shaft 154, at step 237. A coaxial cable (not shown) of probe 800 is connected to the coaxial cable of scanner 150. Scanner 150 is then installed about 4" above new incore housing 706, at step 238.

Probe 800 has a relatively small diameter to fit with appropriate clearance within new incore housing 706. Third probe 800 has several spring-loaded balls 806 on its outer wall. The springs urge the balls outward. The interior wall of the housing presses against these balls, compressing the springs, and thus centering third probe 800 within incore housing 706.

Figure 8B:
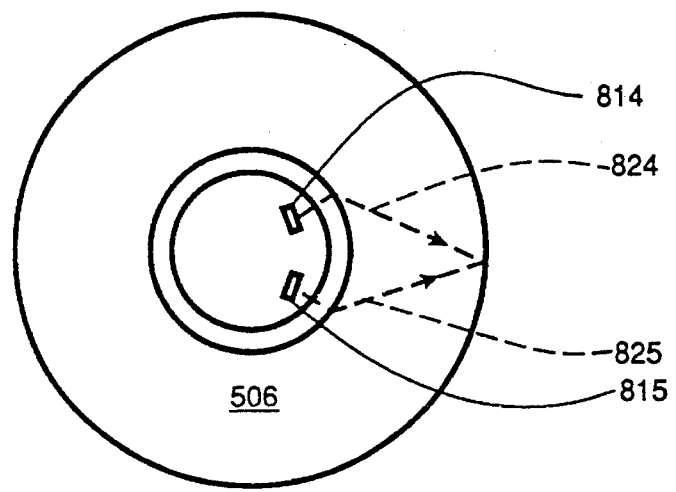
FIG. 8B is a schematic plan sectional view showing beam patterns of the probe of FIG. 8A.

Third probe 800 has five transducers 811–815 providing five beams 821–825. Transducer 811 is oriented so that beam 821 is directed straight into incore housing 706, as indicated in FIG. 8A. Of course all beams include a radial component, but the remaining transducers are characterized by the nonradial component of their beams. Transducer 812 is oriented so that beam 822 is directed upward, and transducer 813 is oriented so that beam 823 is directed downward. Transducer 814 is oriented so that beam 824 is directed clockwise, and transducer 815 is oriented so that beam 825 is directed counterclockwise, as indicated in FIG. 8B.

Scanner 150 drives third probe 800 in a cylindrical raster similar to that used for second probe 600, in this case to ultrasonically examine, at step 239, new housing 706 and J-weld 810 for defects. The rastering of transducers 811–815 provides ultrasonic inspection of the J-weld and adjacent volume of incore housing 706. Scanner 150 and third probe 800 are removed, at step 240, essentially completing third stage 230.

If no defects are detected or once detected defects are corrected, method 200 can proceed to completion. To this end, a coupling tube 902 is inserted laterally to a position vertically between new incore housing 706 and the remainder of incore guide tube 306, as indicated in FIG. 9. Shrink couplings 904 at either end are moved vertically to extend over the adjacent housing and tube. Steam is then applied to shrink couplings 904 to attach the shrink coupling to incore guide tube 306 and new incore housing 706, completing step 241.

At this point, reactor components that were previously removed to facilitate the repair process can be reinstalled or replaced in preparation for restarting reactor 100, at step 242.

Alternative embodiments of the present invention provide for variations in procedure and equipment. Equipment not in use can be removed entirely from the reactor or stored within the reactor for later use. If welding can be performed underwater, water need not be removed from the reactor. Where proper protection is provided, all procedures can be performed without water. Different moderators can be used in place of water. These and other modifications to and variations upon the disclosed embodiments are provided by the present invention, the scope of which is limited only by the following claims.

The invention claimed is:

1. An ultrasonic probe comprising:

a disk-shaped probe head having a plurality of ultrasonic transducers mounted thereon;

a support shaft having an axis and a transverse hole;

means for coupling said probe head to said shaft in a manner whereby said probe head is tiltable about mutually orthogonal first and second axes, said first axis being perpendicular to said shaft axis, wherein said coupling means comprises a sphere-shaped ball having a vertical hole through which said support shaft extends, a transverse hole intersecting said vertical hole, and first and second segments of an annular groove formed in the surface thereof along a great circle through both ends of said vertical hole, and first and second collinear pins slidably seated in said first and second segments of said annular groove respectively, each of said first and second collinear pins being connected to said probe head; and a pin inserted inside said transverse hole in said sphere-shaped ball and said transverse hole in said support shaft for securing said sphere-shaped ball to said support shaft.

2. The probe as defined in claim 1, wherein said plurality of ultrasonic transducers comprises a straight beam transducer and an angled beam transducer, said straight beam transducer being arranged at a first azimuthal position on a bottom surface of said probe head and said angled beam transducer being arranged at a second azimuthal position on said bottom surface of said probe head, said first and second azimuthal positions being separated by a predetermined angle.

3. The probe as defined in claim 1, further comprising a plurality of at least three rollers pivotably mounted on said probe head and spring means for urging said support shaft in a downward direction which is collinear with said shaft axis.

4. The probe as defined in claim 1, further comprising centering means and bearing means, said centering means being rotatably coupled to an end of said support shaft by said bearing means.

5. An ultrasonic probe comprising:

a disk-shaped probe head having at least one ultrasonic transducer mounted thereon;

a support shaft having an axis;

a sphere-shaped ball having a vertical hole through which said support shaft extends, and first and second segments of an annular groove formed in the surface thereof along a great circle through both ends of said vertical hole;

means for securing said sphere-shaped ball to said support shaft; and first and second collinear pins slidably seated in said first and second segments of said annular groove respectively, each of said first and second collinear pins being connected to said probe head wherein said probe head is tiltable about mutually orthogonal first and second axes, said first axis being the axis of said great circle and said second axis being the axis of said first and second collinear pins.

6. The probe as defined in claim 5, wherein said securing means comprises a pin inserted in a hole passing through said sphere-shaped ball and said support shaft.

* * * * *